(12) United States Patent
Baumann et al.

(10) Patent No.: US 7,453,981 B2
(45) Date of Patent: Nov. 18, 2008

(54) FOCUS-DETECTOR ARRANGEMENT WITH X-RAY OPTICAL GRATING FOR PHASE CONTRAST MEASUREMENT

(75) Inventors: Joachim Baumann, München (DE); Martin Engelhardt, München (DE); Jörg Freudenberger, Eckental (DE); Eckhard Hempel, Fürth (DE); Martin Hoheisel, Erlangen (DE); Thomas Mertelmeier, Erlangen (DE); Stefan Popescu, Erlangen (DE); Manfred Schuster, München (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/700,173

(22) Filed: Jan. 31, 2007

(65) Prior Publication Data
US 2007/0183584 A1    Aug. 9, 2007

(30) Foreign Application Priority Data

| Feb. 1, 2006 | (DE) | ........................ | 10 2006 004 604 |
| Feb. 1, 2006 | (DE) | ........................ | 10 2006 004 976 |
| Aug. 9, 2006 | (DE) | ........................ | 10 2006 037 282 |

(51) Int. Cl.
*G01N 23/04* (2006.01)
(52) U.S. Cl. ................... 378/62; 378/4; 378/21
(58) Field of Classification Search ............ 378/21, 378/62, 70, 84, 85, 145, 4
See application file for complete search history.

(56) References Cited

U.S. PATENT DOCUMENTS

| 5,812,629 A | 9/1998 | Clauser |
| 2001/0001010 A1 | 5/2001 | Wilkins |
| 2004/0081218 A1 | 4/2004 | Tabirian et al. |
| 2005/0228271 A1 | 10/2005 | Diebold et al. |
| 2005/0286680 A1 | 12/2005 | Momose |
| 2007/0183560 A1 | 8/2007 | Popescu et al. |
| 2007/0183562 A1 | 8/2007 | Popescu et al. |
| 2007/0183580 A1 | 8/2007 | Popescu et al. |
| 2007/0183581 A1 | 8/2007 | Heismann et al. |

FOREIGN PATENT DOCUMENTS

EP    1 447 046 A1    8/2004

OTHER PUBLICATIONS

Weitkamp et al., "X-ray phase imaging with a grating interferometer", Optics Express 2005, vol. 12, No. 16, pp. 6296-6304.
D. Vaughan (ed.), "X-Ray Data Booklet", Lawrence Berkeley Laboratory, Berkley, 1986, pp. 2-28, 2-29.

(Continued)

*Primary Examiner*—Jurie Yun
(74) *Attorney, Agent, or Firm*—Harness, Dickey & Pierce, P.L.C.

(57) ABSTRACT

A focus-detector arrangement of an X-ray apparatus is disclosed, for generating projective or tomographic phase contrast recordings of a subject. In at least one embodiment, least one grating of a focus-detector arrangement includes, at least partially, a macroscopically homogeneous medium which, when excited by an energy source, assumes a periodic structure/standing wave field that leads to beam splitting and the formation of an interference pattern when the X-ray beam passes through.

30 Claims, 5 Drawing Sheets

OTHER PUBLICATIONS

U. Bonse and M. Hart, "An X-ray Interferometer", Appl. Phys. Lett., 1965, vol. 6, No. 8, pp. 155-156.

Ingal and Beliaevskaya, "X-ray plane-wave topography observation of the phase contrast from a non-crystalline object", J. Phys. D: Appl. Phys. 28, 1995, pp. 2314-2317.

R. Fitzgerald, "Phase-Sensitive X-Ray Interferometer", Physics Today, 53, 2000, pp. 23-26.

Chapman et al., "Diffraction enhanced x-ray imaging", Phys. Med. Biol. 42, 1997, pp. 2015-2025.

Wilkins et a., "Phase-contrast imaging using polychromatic hard X-rays", Nature 384, 1996, pp. 335-338.

V. Lehmann, The Physics of Macropore Formation in low Doped n-Type Silicon, J. Electrochemical Soc. 140 (10), 1993, pp. 2836-2843.

Bergmann, Schäfer, "Lehrbuch der Experimentalphysik", vol. 1, Mechanik, Akustik, Wärme, De Gruyter, Berlin, 1970, pp. 542-554.

Shack et al., J. Opt. Soc. Am. 61, 1971, p. 656.

Platt et al., "History and Principles of Shack-Hartmann Wavefront Sensing", Journal of Refractive Surgery, vol. 17, 2001, pp. 573-577.

F. Roddier, "Variations on a Hartmann theme", Opt. Eng. 29, 1990, pp. 1239-1242.

Primot et al., "Deconvolution from wave-front sensing: a new technique for compensating turbulence-degraded images", J. Opt. Soc. Am. 7(9), 1990, pp. 1598-1608.

J. C. Wyant, "White Light Extended Source Shearing Interferometer", Appl. Opt. 13, 1974, pp. 200-202.

C. L. Koliopoulos, "Radial grating lateral shear heterodyne interferometer", Appl. Opt. 19, 1980, pp. 1523-1528.

J. Primot, L. Songo, "Achromatic three-wave (or more) lateral shearing interferometer". J. Opt. Soc. Am. A, 12(12), 1995, pp. 2679-2685.

J. Primot, "Theoretical description of Shack-Hartmann wave-front sensor", Optics Communications, 222, 2003, pp. 81-92.

V. Ronchi, "Forty Years of History of a Grating Interferometer", Appl. Opt., 3(4), 1964, pp. 437-451.

Schroer et al., "Hard x-ray nanoprobe based on refractive x-ray lenses", Appl. Phys. Lett. 87, 124103, 2005.

M. Bavdaz, N. Gurker, "Coded Imaging X-ray Microprobe", X-Ray Spectrometry, 22, 1993, pp. 65-70.

Momose et al. "Tomographic image reconstruction using X-ray phase information", SPIE, vol. 2708, pp. 674-684.

Barty et al., "Time-gated medical imaging with ultrafast laser plasma x-rays", SPIE, vol. 2523, pp. 286-298.

C. J. Kotre, I. P. Birch, "Phase contrast enhancement of x-ray mammography: a design study", Phys. Med. Biol., 44, 1999, pp. 2853-2866.

Arfelli et al, "Low-dose phase contrast x-ray medical imaging", Phys. Med. Biol. 43, 1998, pp. 2845-2852.

Herrlin et al., "Contrast-Enhanced Radiography by Differential Absorption Using a Laser-Produced X-Ray Source", Investigative Radiology 32, 1997, pp. 306-310.

Grätz et al., "Time-Gated Imaging in Radiology: Theoretical and Experimental Studies", IEEE J. of selected Topics in Quantum Electronics, 2(4), 1996, pp. 1041-1048.

Murnane et al., "Ultrafast X-ray Pulses from Laser-Produced Plasmas", Science, vol. 251, 1991, pp. 531-536.

Krol et al., "Laser-based microfocused x-ray source for mammography: Feasibiliy study", Med. Phys. 24(5), 1997, pp. 725-732.

Piestrup et al., "A design of mammography units using a quasiminichromatic x-ray source", Review of Scientific Instruments, 72(4), 2001, pp. 2159-2170.

C. G. Schroer, B. Lengler, "Focusing Hard X Rays to Nanometer Dimensions by Adiabatically Focusing Lenses", Phys. Rev. Lett. 94, 054802. 2005.

E. Zolotoyabko, J.P. Quitana: "Control of synchroton x-ray diffraction by means for standing acoustic waves", Review of Scientific Instruments, vol. 75, No. 3, Mar. 2004, pp. 699-708.

Claude J. Bailat, Theron J. Hamilton, Christoph Rose-Petruck, Gerald J. Diebold: Acoustic radiation pressure: A "phase contrast" agent for x-ray phase contrast imaging, American institute of Physics, Applied Physics Letters, vol. 85, No. 19, 2004, Aug. 11, 2004, p. 4517-4519.

R. Tuccoulou, O. Mathon, C. Ferrero: "Investigation of surface acoustic wave fields in silicon crystals by x-ray diffraction: A dynamical theory approach", Html abstract—http://jap.aip.org/jap/copyright.jsp, Journal of Applied Physics 97, American Institute of Physics.

Timm Weitkamp et al., X-ray phase imaging with a grating interfeometer, Optics Express, vol. 13, No. 16, published Aug. 8, 2005, pp. 6296-6304.

D.V. Roshchupkin et al,: X-ray Bragg diffraction from langasite crstal modulated by surface acoustic wave, Journal of Applied Physics, vol. 94, No. 10, Nov. 15, 2003, Html: http://jap.aip.org/jap/copyright.jsp.

German Office Action (dated Aug. 10, 2007).

FOCUS-DETECTOR ARRANGEMENT WITH X-RAY OPTICAL GRATING FOR PHASE CONTRAST MEASUREMENT

PRIORITY STATEMENT

The present application hereby claims priority under 35 U.S.C. §119 on German patent application numbers DE 10 2006 004 976.4 filed Feb. 1, 2006, DE 10 2006 004 604.8 filed Feb. 1, 2006, and DE 10 2006 037 282.4 filed Aug. 9, 2006, the entire contents of each of which is hereby incorporated herein by reference.

FIELD

Embodiments of the invention generally relate to a focus-detector arrangement of an X-ray apparatus. For example, it may relate to one for generating projective or tomographic phase contrast recordings of a subject, comprising:
- an X-ray source with a focus, arranged on a first side of the subject, for generating a preferably fan-shaped or conical beam of rays,
- a phase grating arranged on the opposite second side of the subject in the beam path, which generates an interference pattern of the X-radiation in a predetermined energy range, and
- an analysis-detector system which detects at least the interference pattern generated by the phase grating in respect of its phase shift with position resolution

BACKGROUND

Focus-detector arrangements for generating projective or tomographic phase contrast recordings of a subject are generally known. By way of example, reference is made to the European patent application EP 1 447 046 A1 and the German patent applications (not yet published that the priority date of the present application) with the file references 10 2006 017 290.6, 10 2006 015 358.8, 10 2006 017 291.4, 10 2006 015 356.1 and 10 2006 015 355.3.

For imaging by ionizing rays, in particular X-rays, essentially two effects can be observed which occur when the radiation passes through matter, namely absorption and the phase shift of the radiation passing through a subject. It is also known that in many cases, the phase shift when a ray passes through a subject depends much more strongly on small differences with respect to the thickness and composition of the penetrated matter than the absorption does. This allows structures of a subject, in particular the soft structures of a patient, to be recognized better.

For such phase contrast radiography or phase contrast tomography, the phase shift of radiation due to the object must be evaluated. Here, similarly as conventional absorption contrast X-radiography or absorption contrast X-ray tomography, both projective images of the phase shift can be compiled and tomographic representations of the phase shift can be calculated from a multiplicity of projective images.

Such phase shifts can be determined by using interferometric gratings and used for generating projective or tomographic recordings. In respect of these interferometric measurement methods, reference is made to the documents cited above. In these methods, coherent or quasi-coherent X-radiation is passed through a subject, then delivered through a grating with a period matched to the wavelengths of the radiation so that beam splitting takes place first and superposition of the split beams leads to an interference pattern which is modulated by the phase shift due to the object. This interference pattern is measured by a subsequent analysis-detector arrangement, so that the phase shift can be determined. A phase grating is preferably used as the beam splitter.

It is also known to produce such phase gratings, as well as the basic structures of the analyzer gratings, for example by etching rectangular structures from a silicon wafer. A problem with such rigid gratings made of silicon wafers, e.g. phase gratings as beam splitter gratings, amplitude/absorber gratings as analyzer gratings or source gratings, is for example that the accuracy of the structures which can be produced with tolerable outlay is sometimes insufficient. Furthermore, the extent of such silicon wafers is limited by the size of the basic material. Assembling a plurality of sub-pieces can lead to artifacts during the measurement. A further problem is that adaptation to different radiation energies and adaptation of the period and the Talbot distance of the interference pattern is possible only by replacing the relevant gratings.

SUMMARY

In at least one embodiment of the invention, a focus-detector arrangement is provided which comprises gratings that on the one hand can be produced with tolerable costs, and on the other hand can be readily adapted to different radiation energies, permit variation of the period of the phase grating and therefore of the interference pattern as well as variation of the Talbot distance, without having to carry out replacement of the gratings, and lastly are subject to the least possible limitations in respect of their surface extent.

The Inventors have discovered that for making radiation optical or X-ray optical gratings, it is sufficient to induce periodic structure differences in a material used as a grating material in order to achieve the desired grating effects. For example, periodically different mass concentrations, different structures or different density may be used for this. Such periodic structure differences are created, for example, by an energy source, such as by the generation of standing ultrasound waves in a material or medium or on its surface for example, which lead to periodically recurring differences in the structure and/or mass concentration or density of the material depending on the consistency of the material, and therefore induce the desired grating properties of this material. To this end, for example, acoustic standing waves in gas cells, surface acoustic standing waves in liquids and surface acoustic standing waves in a solid material may be used.

In principle, there are the following variants for matching the period and amplitude in such variable gratings:
(i) Varying the period/spatial frequency of the X-ray interference pattern by varying the grating period of the ultrasound grating which functions as a phase grating, or varying the frequency of the exciting ultrasound by varying the frequency of the electrical control signal
(ii) Varying the resonant energy of the phase grating and therefore of the X-ray interference pattern by varying the grating amplitude of the ultrasound grating which functions as a phase grating, or varying the amplitude/intensity of the exciting ultrasound by varying the voltage of the electrical control signal
(iii) Varying the absorption/modulation of the ultrasound grating which functions as an analyzer grating/amplitude grating by varying the amplitude/intensity of the exciting ultrasound by varying the voltage of the electrical control signal.

In at least one embodiment, the Inventors propose that a focus-detector arrangement known per se of an X-ray apparatus for generating projective or tomographic phase contrast recordings, having an X-ray source with a focus, arranged on a first side of the subject, for generating a preferably fan-shaped or conical beam of rays, a phase grating arranged on the opposite second side of the subject in the beam path, which generates an interference pattern of the X-radiation in a predetermined energy range, and having an analysis-detector system which detects at least the interference pattern generated by the phase grating in respect of its phase shift with position resolution and determines the phase shift therefrom with position resolution, should be improved so that that at least one grating of the focus-detector arrangement consists at least partially of a macroscopically homogeneous medium (=grating medium) which, when excited by ultrasound, comprises periodic structure variations that lead to interference phenomena in the X-ray beam when the X-ray beam passes through.

According to at least one embodiment of the invention, the grating medium of at least one grating may be gaseous or liquid, in which case the liquid may for example also consist of a suspension. While density differences of the same material are essentially generated by a standing ultrasound wave in gas, liquid and a solid body, a non-equidistribution of the solid substance and therefore in turn a density difference can be generated in a suspension. In a similar way, the particles in the known sound patterns of sawdust or the like accumulate in the region of the wave nodes, while the wave antinodes remain substantially free from particles.

In another variant according to at least one embodiment of the invention, the grating medium may consist of a gel. Like a liquid or gas, this grating medium adapts readily to predetermined geometrical shapes. The gel may furthermore comprise thixotropic properties, which lead to amplification of periodic structure differences.

Another variant of at least one embodiment resides in the grating medium of the at least one grating being a solid body. This may particularly preferably be a piezoelectric material, in which case this piezoelectric material itself may also be used for the ultrasound generation.

It is furthermore proposed, in at least one embodiment, that the grating medium of at least one grating be arranged in a closed space, which includes a first ultrasound generator on at least one side for generating the standing ultrasound waves in the grating medium. To this end, for example, an ultrasound reflector may be arranged on the opposite side. It is also possible to arrange a second ultrasound generator on the opposite side so that, with appropriate mutual tuning of the two ultrasound generators, a standing wave field can then be generated in the grating medium. The at least one ultrasound generator should preferably be mechanically coupled directly to the grating medium.

An ultrasound generator generates a traveling ultrasound wave. A standing wave is obtained therefrom by interference with a second ultrasound wave of the same wavelength. The second wave is generated most simply by reflecting the first wave from a wall. As an alternative, it may also be generated by a second generator lying opposite.

Within the focus-detector arrangement according to at least one embodiment of the invention, such a grating according to the invention may be used as a phase grating (=beam splitter) or as an amplitude grating (source grating, analyzer grating). Such a phase grating may also have a radius of curvature around the focus in at least one section plane. In the simplest form, the grating medium is bounded in the transmission direction by plane parallel walls of a gas cell. For a cone beam geometry or fan beam geometry, the walls may have the shape of cylinder segments or spherical caps.

Corresponding to the use of this grating, it is furthermore required, in at least one embodiment, that this grating fulfill at least one of the following geometrical relationships:

$$g_2 = \frac{1}{2} \cdot \frac{r_2}{r_1} \cdot g_1, \quad (1)$$

$$r_1 > \frac{g_1^2}{2\lambda}, \quad (2)$$

$$r_2 - r_1 = d_m = \left(m - \frac{1}{2}\right) \cdot \frac{g_1^2}{4 \cdot \lambda}, \quad (3)$$

where:
$r_1$=radial distance from the focus to the phase grating;
$r_2$=radial distance from the focus to the analysis-detector system;
$g_1$=period of the phase grating ($G_1$);
$g_2$=period of the analysis-detector system for the phase detection.
$\lambda$=wavelength of the X-radiation in question;
$d_m$=distance from the phase grating to the analysis-detector system=$m^{th}$ order Talbot distance.

In another refinement of the focus-detector arrangement according to at least one embodiment of the invention, the Inventors propose that the focus be of substantially point-like design, although on the other hand it is also possible to design the focus so that it is two-dimensional and arrange a source grating for generating a beam of coherent rays between the focus and the subject, in order to achieve a field with coherent X-rays emerging there. Such a source grating may also be formed according to the invention by a grating medium excited with ultrasound, in which case this may have any of the particular features presented above.

The Inventors, in at least one embodiment, furthermore propose that the analysis-detector system be formed as a combination of a position-resolving detector having a multiplicity of detector elements, the size of which determines the position resolution of the system, and an analyzer grating upstream in the radiation direction for determining the average phase shift of the X-radiation per detector element.

In such an analysis-detector system, the detector and/or the analyzer grating of the analysis-detector system may again have a curvature around the focus.

If such an analysis-detector system is used, then at least the one grating of the focus-detector arrangement according to at least one embodiment of the invention, which is formed by a grating medium excited with ultrasound, may be the analyzer grating itself.

In respect of these particular embodiments with a combination of an analyzer grating and a downstream detector, reference is made in particular to the patent applications cited above with the file references DE 10 2006 015 358.8, 10 2006 015 356.1 and 10 2006 015 355.3, the entire contents of each of which is hereby incorporated herein by reference. It should in particular be pointed out that the replacement of X-ray optical gratings may be carried out by merely having to generate different standing waves with different wavelengths according to at least one embodiment of the invention. This may for example be done by changing the wavelength which is generated by the ultrasound, while the distance between the ultrasound generator and the opposite reflector remains an integer multiple of the wavelength, i.e. the wavelength is changed in particular increments.

Another possibility for fine tuning of the wavelength or period of the grating is to change the distance between the ultrasound generator and the opposite reflector, or the second ultrasound generator, only slightly so that corresponding adaptation is carried out for the respectively desired period. Such a change of the resonator length of the ultrasound in the grating medium may, for example, be performed by applying at least one piezo element.

In another alternative embodiment of the focus-detector arrangement, it is proposed that the analysis-detector system be formed as a position-resolving detector having a multiplicity of detector elements, which determine the position resolution of the system, at least some of the detector elements comprising an internal structure which is suitable for determining the average phase shift of the X-radiation of a particular energy per detector element.

With respect to this embodiment of the analysis-detector system, reference is made in particular to the documents DE 10 2006 017 290.6 and DE 10 2006 017 291.4 cited above (not yet published at the priority date of the present application), the entire contents of each of which is hereby incorporated herein by reference.

In the context of at least one embodiment of the invention, such focus-detector arrangements may for example be used for X-ray systems to generate purely projective phase contrast recordings or for X-ray C-arc systems with which projective and tomographic phase contrast recordings can be compiled, or else for pure X-ray CT systems to generate tomographic phase contrast recordings.

According to the inventive concept of at least one embodiment, the Inventors also provide a method for operating an X-ray system for generating projective and/or tomographic phase contrast recordings, in which a focus-detector arrangement having the features described above is used, wherein a relative position change of the grating lines, necessary for measuring the phase shift of the X-radiation in the analysis-detector system, is generated by modifying the "standing" ultrasound wave field.

A modification or displacement of the standing ultrasound field may be generated by:
  modification of the exciting ultrasound frequency,
  modification of the distance between two opposite ultrasound generators or between an ultrasound generator and an ultrasound reflector,
  phase shifting between two opposite ultrasound generators that excite the standing wave,
  mechanical displacement of the entire grating.

In connection with at least one embodiment of the invention, the following facts regarding the problem of "coherent X-radiation", "coherent X-radiation sources" and "quasi-coherent X-radiation sources" should also essentially be pointed out in the context of at least one embodiment of the invention:

The emission of X-ray photons from laboratory X-ray sources (X-ray tubes, secondary targets, plasma sources, radioactive sources) as well as by conventional synchrotron radiation sources of the first to third generations is subject to stochastic processes. The emitted X-radiation therefore has no spatial coherence per se. In phase contrast radiography and tomography or any interference experiment, however, the radiation of X-ray sources behaves as coherent radiation when the observation angle at which the source appears to the observer or the object, the grating or the detector, is sufficiently small. The so-called lateral coherence length L can be provided as a measure of the spatial coherence of an extended X-ray source:

$$L = \lambda \frac{a}{s}. \tag{4}$$

Here, $\lambda$ is the wavelength, s is the transverse source size and a is the source-observer distance. Many authors also refer to half the above-defined value as the spatial coherence length. The exact value is incidental; what is important is that the coherence length L is large compared to the (lateral) dimension of the spatial region from which rays are intended to interfere with one another.

In the context of the patent application, the term coherent radiation is intended to mean radiation which, under the given geometries and distances, leads to the desired X-ray optical grating for forming an interference pattern. It is self-evident that the spatial coherence and therefore the spatial coherence length is always determined by the trio of quantities: wavelength, source size and observation distance. With a view to compact formulation, this fact has been abbreviated to terms such as "coherent X-radiation", "coherent X-radiation source" or "point source for generating coherent X-radiation". The basis for these abbreviations is that the wavelength or the energy E of the X-radiation in the applications discussed here is limited by the desired penetratability of the subject on the one hand and the spectrum available in laboratory X-ray sources on the other hand. The distance a between the source and the observer is also subject to certain restrictions in laboratory equipment for nondestructive material testing or medical diagnosis. This usually leaves only the source size s as a last degree of freedom, even though the relationships between source size and tube power set narrow limits here.

The source grating makes it possible to use larger and therefore higher-power X-ray sources. The narrow slits of the source grating ensure that all the rays, which have to emerge from the same slit, comply with the requisite spatial coherence. Only photons from one slit can interfere with one another, i.e. be superposed with correct phase. Although no correctly phased superposition is possible between the photons from slit to slit of the source grating, with suitable tuning of the source grating period $g_0$ and the interference pattern period $g_2$ as well as the distance l between the source grating $G_0$ and the phase grating $G_1$ and the distance d between the phase grating $G_1$ and the interference pattern $G_2$ according to $g_0/g_2=l/d$, correct superposition of the wave antinodes and the wave nodes of the standing wave field is possible at least in respect of intensity. In the abbreviated formulation of the patent application, the term "quasi-coherent radiation" or "quasi-coherent radiation source" is used in this context.

The temporal or longitudinal coherence of the radiation is associated with the monochromaticity of the X-radiation or of the X-radiation source. The X-radiation of intense characteristic lines usually has a sufficient monochromaticity or temporal coherence length for the applications discussed here. Upstream monochromators or selection of the resonant energy via the bar height of the phase grating can also filter out a sufficiently narrow spectral range from a Bremsstrahlung spectrum or synchrotron spectrum, and thus satisfy the requirements for the temporal coherence length in the present arrangements.

BRIEF DESCRIPTION OF THE DRAWINGS

The invention will be explained in more detail below with reference to example embodiments with the aid of the figures, only the features necessary for understanding the embodiments of the invention being represented. Here, unless explicitly mentioned, the following references are used: 1: CT system; 2: first X-ray tube; 3: first detector; 4: second X-ray tube; 5: second detector; 6: gantry housing; 7: patient; 8: patient support; 9: system axis; 10: control and computation unit; 11: memory; 12: gas cell; 13: gas; 14: ultrasound generator; 15: standing wave; 16: ultrasound reflector; 17: liquid; a: the size of a voxel; $D_1$: detector; d: Talbot distance=distance from the phase grating to the interference maxima or to the analysis-detector system; $E_i$: detector elements; $F_1$: focus; G: grating; $G_0$: source grating; $G_1$: phase grating; $G_2$: analyzer grating; $g_1$: period of the phase grating $G_1$; $g_2$: period of the analysis-detector system with respect to phase detection; h: thickness of the gas volume of a gas cell; $I(E_i(X_G))$: measured intensity at the detector element $E_i$ with the grating offset $X_G$; $I_{ph}$: radiation intensity; $L_c$: coherence length; l: distance between gratings $G_0$ and $G_1$; n: refractive index; P: sample; $Prg_x$: program; w: extent of the focus; $X_G$: offset of the grating in the x direction; x, y, z: Cartesian coordinates; $Prg_n$: program; $S_i$: X-rays; φ: phase shift; $φ_{EX}$: phase of the sinusoidal intensity profile at the detector element $E_x$; $φ_{ij}$: relative phase shift between the detector elements $E_i$ and $E_j$; λ: wavelength of the energy of the X-radiation in question; δ: real decrement of the refractive index, here of the grating medium; Λ: ultrasound wavelength.

In detail.

DETAILED DESCRIPTION OF THE EXAMPLE EMBODIMENTS

Figure 1:
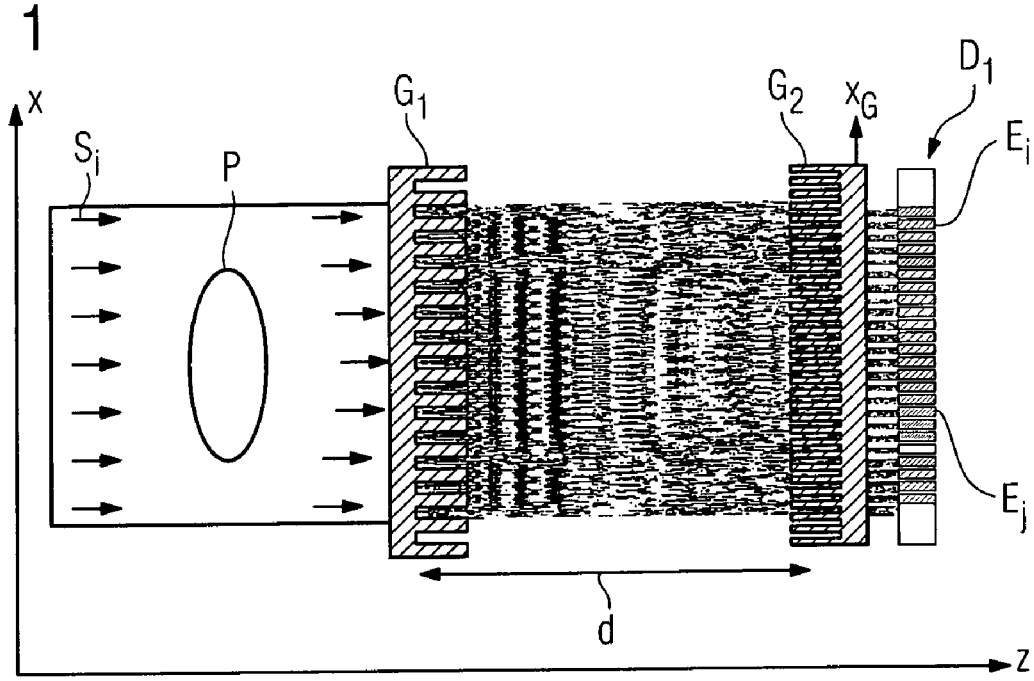
FIG. 1: shows a longitudinal section through an outline representation of a focus-detector arrangement with a phase grating as the beam splitter, an analyzer grating and a detector for representing the interference phenomenon.

It will be understood that if an element or layer is referred to as being "on", "against", "connected to", or "coupled to" another element or layer, then it can be directly on, against, connected or coupled to the other element or layer, or intervening elements or layers may be present. In contrast, if an element is referred to as being "directly on", "directly connected to", or "directly coupled to" another element or layer, then there are no intervening elements or layers present. Like numbers refer to like elements throughout. As used herein, the term "and/or" includes any and all combinations of one or more of the associated listed items.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath " other elements or features would then be oriented "above " the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the " are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

For better understanding, the basic principle of phase contrast measurement will be described below with FIGS. 1 to 3.

Figure 2:
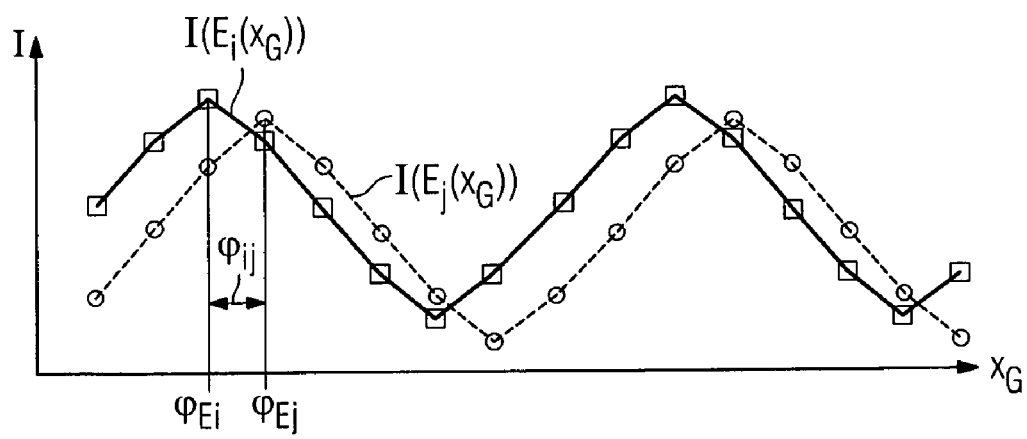
FIG. 2: shows the intensity profile of selected detector elements as a function of the transverse relative position of the analyzer grating with respect to the interference pattern.

FIG. 1 shows quasi-coherent radiation coming from the focus or individually coherent radiation coming from a source grating, which passes through a sample P, phase shift phenomena taking place after it has passed through the sample P. When passing through the grating $G_1$ an interference pattern is thereby generated, as represented by the gray shading, which with the aid of the grating $G_2$ leads to different radiation intensities per detector element on the downstream detector $D_1$ and its detector elements, an interference pattern or X-ray standing wave field being formed. If the detector element $E_i$ for example is considered as a function of a displacement $X_G$ of the analyzer grating $G_2$ and the intensity $I(E_i(X_G))$ as a function of the lateral displacement $X_G$ is plotted against the intensity $I_{ph}$, then a sinusoidal profile of the intensity $I(E_i(X_G))$, $I(E_j(X_G))$ is obtained for each detector element $E_i$; $E_j$ as shown in FIG. 2. The phase angle $φ_{Ei}$, $φ_{Ej}$ can be determined for each detector element $E_i$; $E_j$ from these functions. Comparing the phase angles $\phi_{Ei}$, $\phi_{Ej}$ of neighboring pixels yields the mutual relative phase shift $\phi_{i,j}$.

The mutual phase shift $\phi$ can be determined for each detector element from the functions. The following applies:

$$\varphi = 2\pi n \frac{a}{\lambda}, \quad (5)$$

where $\alpha$ corresponds to the size of a voxel or pixel in the examined object, n is its refractive index and $\lambda$ represents the wavelength of the X-radiation.

Relative phase shifts of less than $2\pi$ can be determined in this way. If the phase shift of an object is more than $2\pi$, then, from a region in which there is no phase shift, it is necessary to integrate the differential phase shifts into the desired region as far as the desired position of the object. A projective pixel image or, by corresponding reconstruction methods, even a volume image can be compiled from the phase shifts determined in this way.

It should be pointed out that here, with a variable ultrasound-tunable grating, the term position of the grating does not necessarily mean the position of the outer walls but the position of the wave antinodes or pressure maxima and wave nodes or pressure minima transversely to the optical axis.

For each ray in space, the phase shift per ray can therefore be determined by at least three measurements with a respectively offset analyzer grating, from which either the pixel values of a projective recording can be calculated directly in the case of projective X-ray recordings, or projections whose pixel values correspond to the phase shift or to the absorption values can be compiled in the case of a CT examination, so that with the aid of reconstruction methods known per se it is possible to calculate therefrom which volume element in the subject is to be ascribed to which component of the measured phase shift. Section images or volume data are thus calculated therefrom, which reflect the local effect of the examined object in respect of the X-ray phase shift and the X-ray absorption. Since even minor differences can exert a strong effect on the phase shift in this context, very detailed and high-contrast volume data can thereby be obtained from materials which are relatively similar per se, in particular soft tissue.

This variant of detecting phase shifts of the X-rays which pass through a subject, with the aid of a multiply offset analyzer grating and measuring the radiation intensity on a detector element behind the analyzer grating, means that at least three measurements of each X-ray have to be carried out with an analyzer grating respectively displaced by fractions of the period of the interference pattern.

In principle, it is even possible to make do without such an analyzer grating and use a sufficiently fine-structured detector instead, in which case the dose losses due to absorption in the bars of the analyzer grating are obviated and the phase shift in the relevant ray can be determined by a single measurement.

In order to measure the phase contrast, it is necessary to use coherent radiation or at least quasi-coherent radiation. This may be generated for example by a point-like focus or as a field of individually coherent beam sources by a source grating behind a focus, which is designed to be two-dimensional, or by a grating-like configured focal spot on an anode.

In the case of the latter "multi-strip source " or a source grating, the source size of the individual strip or of the source grating individual slit must be used for calculating the coherence length. In the case of the strip source, only the photons which come from a single strip require a sufficient coherence length. The photons from strip to strip do not need to have this coherence. In the case of the periodic grating, it is sufficient here that each strip per se generates an interference pattern. The interference patterns of the various strips are superposed only in terms of intensity. Consequently, there does not need to be any coherence between the photons from the various strips.

Figure 3:
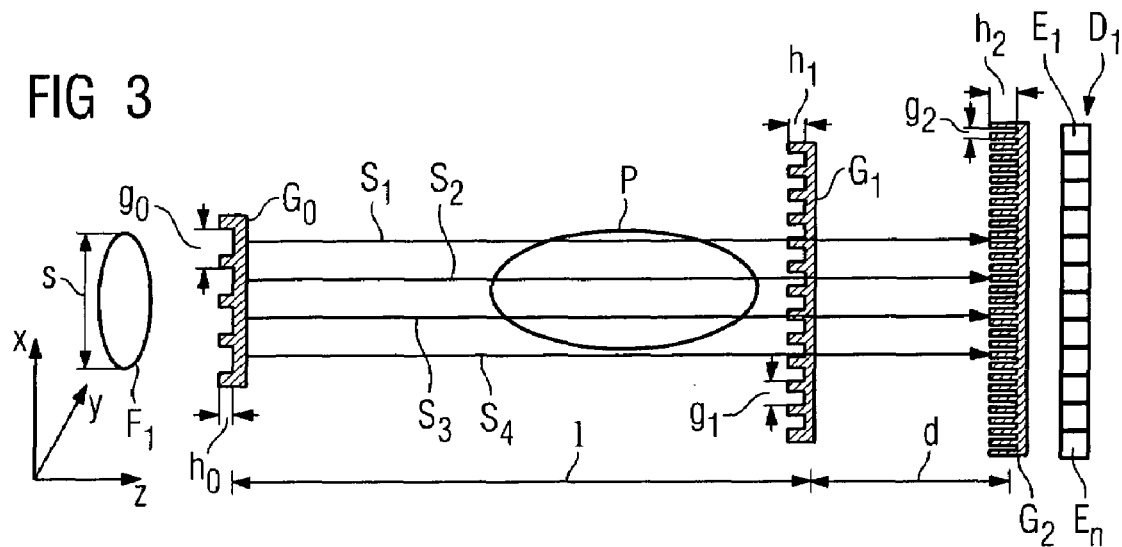
FIG. 3: shows a longitudinal section through a focus-detector system, with the arrangement of the source grating, the phase grating and the analyzer grating.

Such a variant, in which a field of individually coherent radiation is generated by a source grating behind a focus designed to be two-dimensional, is schematically shown in FIG. 3 by a focus-detector system with a grating set $G_0$ to $G_2$. In principle all gratings represented there may be replaced by gratings according to an embodiment of the invention The first grating $G_0$ is preceded by the focus $F_1$ with a lateral extent. The first grating $G_0$ has a grating line period go and a grating bar height $H_0$. Correspondingly, the gratings $G_1$ and $G_2$ are also provided with a height $h_1$ and $h_2$, respectively and a period $g_1$ and $g_2$, respectively. In order for the phase measurement to function, it is necessary that the distance l between the gratings $G_0$ and $G_1$ and the distance d between the gratings $G_1$ and $G_2$ should be in a particular mutual ratio. Here $$g_0 = g_2 \frac{l}{d}. \quad (6)$$

The distance of the detector $D_1$ with its detector elements $E_1$ to $E_n$ from the analyzer grating $G_2$ is not critical, although it should be selected to be as short as possible in order to avoid intensity losses and crossover effects. The height $h_1$ of the bars of the phase grating should be selected so that the following formula is satisfied according to the wavelengths in question, i.e. the relevant energy of the X-radiation, and in relation to the respective grating material:

$$h_1 = \frac{\lambda}{2(n-1)}. \quad (7)$$

Here, n denotes the refractive index of the grating material and $\lambda$ denotes the wavelengths of the X-rays, at which the phase shift is intended to be measured. This grating may advantageously be adjusted to an energy which corresponds to a characteristic line in the X-ray spectrum of the anode being used; at least, a sufficient photon flux should be available in this energy range. With the nowadays customary tungsten anodes, for example, the $K\alpha$ line may be used. It is nevertheless also possible to use the $K\beta$ line lying next to it. When other anode materials are selected (for example Cu, Mo, Ag, etc.), different energies and therefore different dimensioning of the phase grating will correspondingly be necessary. L or M lines can also be used in principle. Besides the characteristic lines, certain ranges of the Bremsstrahlung spectrum may also be used.

The height $h_2$ of the analyzer grating must be sufficient in order to generate effective absorption differences between the bars through which the X-radiation passes and the substantially free positions of the grating, in order to obtain a corresponding interference pattern or X-ray standing wave field on the rear side.

The line orientation of the gratings $G_0$ to $G_2$ is regularly configured so that the grating lines of the gratings provided, and optionally provided strip structures of the detector elements, extend mutually parallel. It is furthermore advantageous, but not necessary, that the grating lines should be oriented parallel or perpendicularly to the system axis S.

An embodiment of the invention now proposes that at least one grating of the focus-detector arrangement consist at least partially of a macroscopically homogeneous medium (=grating material) which, when excited by an energy source, such as ultrasound for example, includes periodic structure variations that affect the transmitted radiation like an X-ray optical grating and correspondingly lead to interference patterns.

To this end three different alternative embodiments are proposed by way of example, all of which are capable of varying the grating periods.

Figure 4:
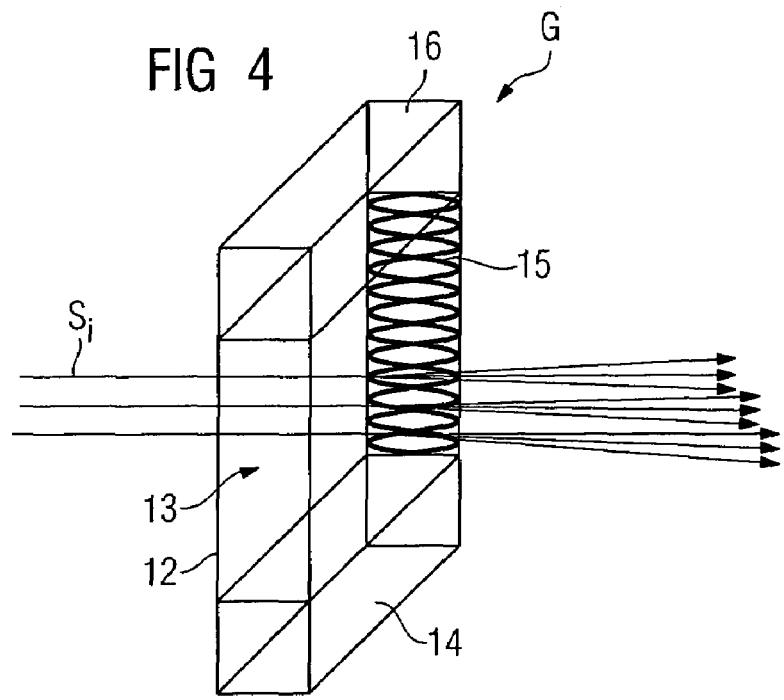
FIG. 4: shows a three-dimensional outline representation of an X-ray optical grating with gas as the ultrasound-excited grating medium.

A) Acoustic standing wave field in gas cells as diffraction gratings:

FIG. 4 shows a variant according to an embodiment of the invention in which the acoustic standing waves, or ultrasound standing waves, with high pressure amplitudes in gas cells generate diffraction gratings for X-rays. Here, the grating G is formed by a cell 12 in which there is a gas 13 as the grating medium. An ultrasound generator 14 is arranged on one side of the cell 12, opposite which there is an ultrasound reflector 16 on the other side. Between the ultrasound generator 14 and the ultrasound reflector 6 it is therefore possible to generate a standing ultrasound wave field 15 which acts as a grating with the period of one half the ultrasound wavelength. In this way, both phase gratings and amplitude/absorption gratings can be formed by acoustic ultrasound standing waves in gas cells. The cells should be gastight.

In respect of a flat cell, this should be formed substantially rectangularly and the walls perpendicular to the beam direction should be mutually parallel and as far as possible of equal thickness. In the case of cells curved around the focus, the walls perpendicular to the beam direction should be configured concentrically and equidistant and should also be of constant thickness.

In both variants of the cell, the ultrasound generator and the ultrasound reflector should lie opposite one another, although in a curved cell these two elements need not necessarily be aligned mutually parallel but may be at an angle to one another, which could for instance correspond to the fan angle of a fan beam being used. It is also possible for these elements to be arranged in the fan plane. For the ultrasound reflector, a high reflection coefficient is desirable in order to obtain an unattenuated acoustic standing wave field, i.e. an intense standing wave field with high pressure amplitudes compared to the average gas pressure. The ultrasound generator propagates the sound intensity through the reflecting waves of the acoustically excited gas cell. As an alternative, it is also possible to use a further ultrasound generator instead of the ultrasound reflector, in which case the two ultrasound generators must be tuned to one another in phase and frequency so as create the desired standing wave field.

If the acoustically excited gas cell is intended to generate a phase grating for X-rays, then a major requirement of the layout of a gas cell for acoustic standing waves is to achieve a sufficient or the correct phase shift. In the ideal case, a phase change of $\pi$ should be achieved between the nodes and antinodes of the acoustic standing waves.

A phase shift of $\pi$ will be obtained when the thickness h of the gas volume, which is exposed to the acoustic standing wave field, fulfills the following condition:

$$h = \frac{\lambda}{2\delta}, \quad (8)$$

where $\delta$ is the real decrement of the refractive index of the gas due to the pressure amplitude and $\lambda$ is the X-ray wavelength. For high photon energies $E \gg E_K$ or short wavelengths $\lambda \ll \lambda_K$, i.e. for photon energies above the K shell electron binding energy of the gas, the following applies to an approximation for the real decrement $\delta$ $$\delta = \frac{r_0 N_A \rho Z \lambda^2}{2\pi A_r}, \quad (9)$$

where $r_0$ is the classical electron radius, $N_A$ is Avogadro's number, Z is the atomic number of the gas atoms, $A_r$ is the relative atomic mass of the atoms of the gas. In an ideal gas, this expression reads:

$$\delta = \frac{r_0 N_A p Z \lambda^2}{2\pi R_0 T_0}, \quad (10)$$

where p is the gas pressure, $R_0$ is the gas constant and $T_0$ is the absolute temperature of the gas. In the case of nonideal gases close to the triple point, it is necessary to use equations for real gases or tabulated values.

In the acoustic standing wave field of the gas cell, the phase shift difference between the nodes and the antinodes also depends on the pressure differences which are generated in the gas cell by the ultrasound generator. The pressure amplitude $\Delta p$ in an acoustic standing wave is given by:

$$\Delta p = \sqrt{8 J \rho c}, \quad (11)$$

where J is the sound intensity [W/m²], $\rho$ is the thickness of the gas and c is the velocity of sound. The effective phase shift corresponds to the difference in $\delta$ between the nodes and the antinodes, i.e. the pressure amplitude $\Delta p$.

By using all these equations, the thickness of the gas volume for a phase shift of $\pi$ under the given conditions can be obtained and adjusted to the desired value by using the variable parameters.

In order to keep the thickness of the gas volume small, so that nonuniform pressure fluctuations and edge effects can be neglected, gases with a high density should be selected. A high gas density also permits better adaptation of the characteristic impedance of a generator to the characteristic impedance of the gas. Suitable gases are for example Xe, $SF_6$ and $WF_6$. Under pressure, however, other gases could also be used.

In any event the period of the acoustic standing wave field is given by the frequency, which is generated by the ultrasound generator, and the velocity of sound in the gas volume. The velocity of sound c in gases depends on the gas pressure p, the gas density $\rho$ and the type of gas, specifically according to $$c = \sqrt{\frac{p\kappa}{\rho}}, \quad (12)$$

where κ is the adiabatic exponent of the gas. The wavelength Λ of the sound wave in the gas, i.e. the periodicity of the acoustic standing wave, for the sound frequency ν is given by:

$$\Lambda = c/\nu.$$

By using ultrasound in the MHz and GHz frequency ranges, an acoustic standing wave field can be generated with a period in the range of a few μm, which is suitable for the applications mentioned in the introduction. The acoustic wavelength Λ respectively defines the period g of the grating according to g=Λ, and specifically both in the beam splitter grating/phase grating G1 as well as in the analyzer grating/absorber grating $G_2$ and in the source grating $G_0$, so that no differentiation is required with regard to the period in the description. When using acoustically excited gas cells as an analyzer or absorber grating for X-rays, however, it is necessary to ensure the correct absorption. In the ideal case, the absorption at the wave antinodes should be as high as possible and vanish at the wave nodes, i.e. tend toward zero.

Figure 5:
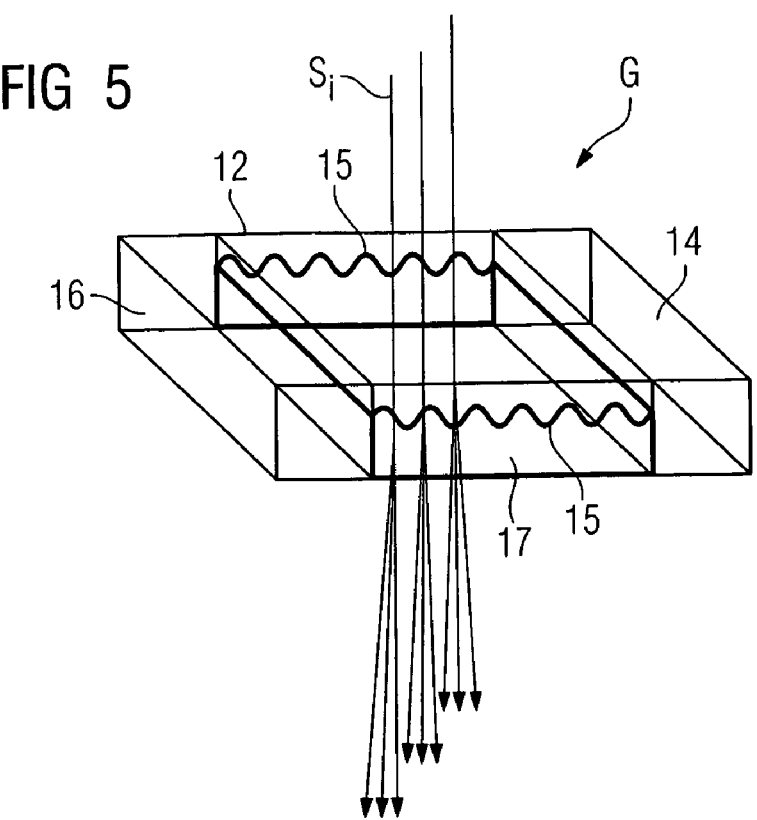
FIG. 5: shows a three-dimensional outline representation of an X-ray optical grating with liquid as the ultrasound-excited grating medium.

B) Surface acoustic standing waves in liquids as diffraction gratings:

As an alternative, acoustic standing waves or ultrasound standing waves in liquid cells with an open surface are proposed as diffraction gratings for X-rays. An example embodiment is represented in FIG. 5.

There, the grating G is formed by a cell 12 in which there is a liquid 17 as the grating medium. Here again there is an ultrasound generator 14 on one side of the cell 12, opposite which there is an ultrasound reflector 16 on the other side. Between the ultrasound generator 14 and the ultrasound reflector 16, it is therefore possible to generate a standing wave 15 which acts as a grating with a period of one half the wavelength of the ultrasound.

Such cells 12 must be liquid-tight. For a parallel beam geometry, the cell should as far as possible have a cuboid configuration, with the ultrasound generator and the ultrasound reflector or a further ultrasound generator facing one another on two opposite sides. A characteristic impedance adapter (not represented in detail) may be positioned between the ultrasound generator and the liquid, although such a characteristic impedance adapter is not categorically necessary for coupling ultrasound into liquids.

The waves on the surface cause phase shifts for X-rays passing through. So that a maximal intensity is obtained in $+1^{st}$ and $-1^{st}$ order rays, the height of the waves should induce a phase shift of π. With typical liquid densities of 1 g/cm³, waves several μm high are sufficient for this. In detail, the suitable wave height can be calculated with the aid of Equations (8) and (9) as given above.

The periodicity or spatial frequency is given by the frequency of the ultrasound generator and the specific velocity of sound in the selected liquid for the selected frequency according to Equation (13). Wave periods in the μm range can be achieved with ultrasound frequencies in the kHz and MHz ranges.

Figure 6:
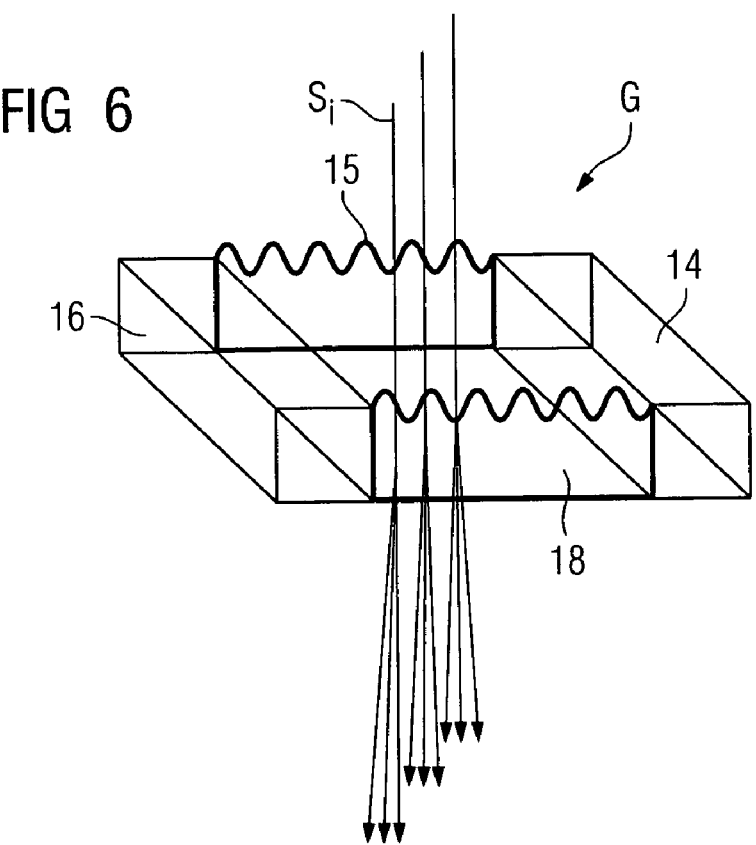
FIG. 6: shows a three-dimensional outline representation of an X-ray optical grating with a solid body as the ultrasound-excited grating medium.

C) Surface acoustic standing waves in a solid material as diffraction gratings:

According to a further alternative, a solid medium is also proposed as the grating medium. Such an embodiment is represented in detail in FIG. 6. A special cell is not categorically necessary here, since the grating medium may already be configured so that it is geometrically stable. In the example represented, the grating medium G designed as a solid body is excited to form a standing wave 15 by an oppositely arranged ultrasound generator 14 and ultrasound reflector 16. As an alternative, however, it is also possible to use a piezoelectrically active grating medium which itself generates the oscillations.

Piezoelectric material, for example quartz ($SiO_2$), lead zirconium titanate (abbreviated to PZT) $Pb(Zr,Ti)O_3$, $LiNbO_3$, $LiTaO_3$, ZnO, is highly suitable for converting electrical signals into sound/ultrasound oscillations in the kHz, MHz or GHz range. For this purpose, the orientation of the exciting electric field and the cross section of the crystal must be matched to one another so as to take into account the piezoelectric tensor properties, in order to optimize the sound/ultrasound oscillations.

As an alternative, such a grating medium may be used to produce a conventional X-ray optical grating, in which case a continuous variation of the grating period in the fine range can be achieved through the length variation properties of the piezoelectric material.

Figure 7:
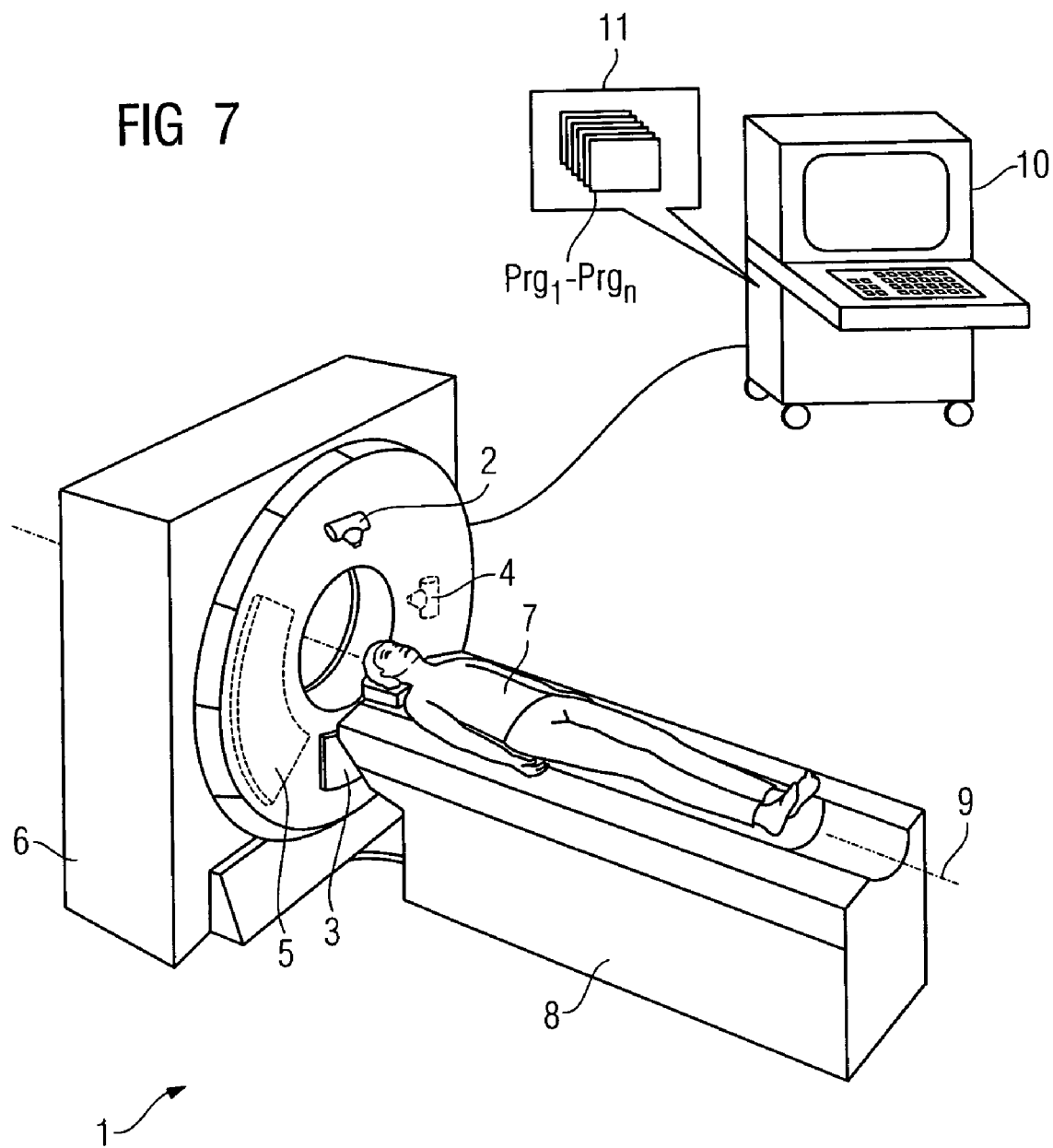
FIG. 7: shows an X-ray CT system in 3D view with a focus/detector system according to an embodiment of the invention.

FIG. 7 represents a complete computer CT system with focus-detector systems according to an embodiment of the invention for carrying out the method according to an embodiment of the invention, by way of example and also generically for other X-ray systems, in particular X-ray systems for generating projective phase contrast recordings and for C-arc equipment. This figure shows the CT system 1 which comprises a first focus-detector system with an X-ray tube 2 and a detector 3 lying opposite, which are arranged on a gantry (not represented in detail) in a gantry housing 6. A grating system according to FIGS. 1 to 3 is arranged in the beam path of the first focus-detector system 2, 3 so that the patient 7, who lies on a patient support 8 displaceable along the system axis 9, can be displaced into the beam path of the first focus-detector system and scanned there. The CT system is controlled by a computation and control unit 10 in which programs $Prg_1$ to $Prg_n$ are stored in a memory 11, which carry out the method according to the invention as described above and reconstruct corresponding tomographic images from the measured ray-dependent phase shifts.

Instead of a single focus-detector system, a second focus-detector system may optionally be arranged in the gantry housing. This is indicated in FIG. 7 by the X-ray tube 4 shown in dashes and the detector 5 represented in dashes.

Figure 8:
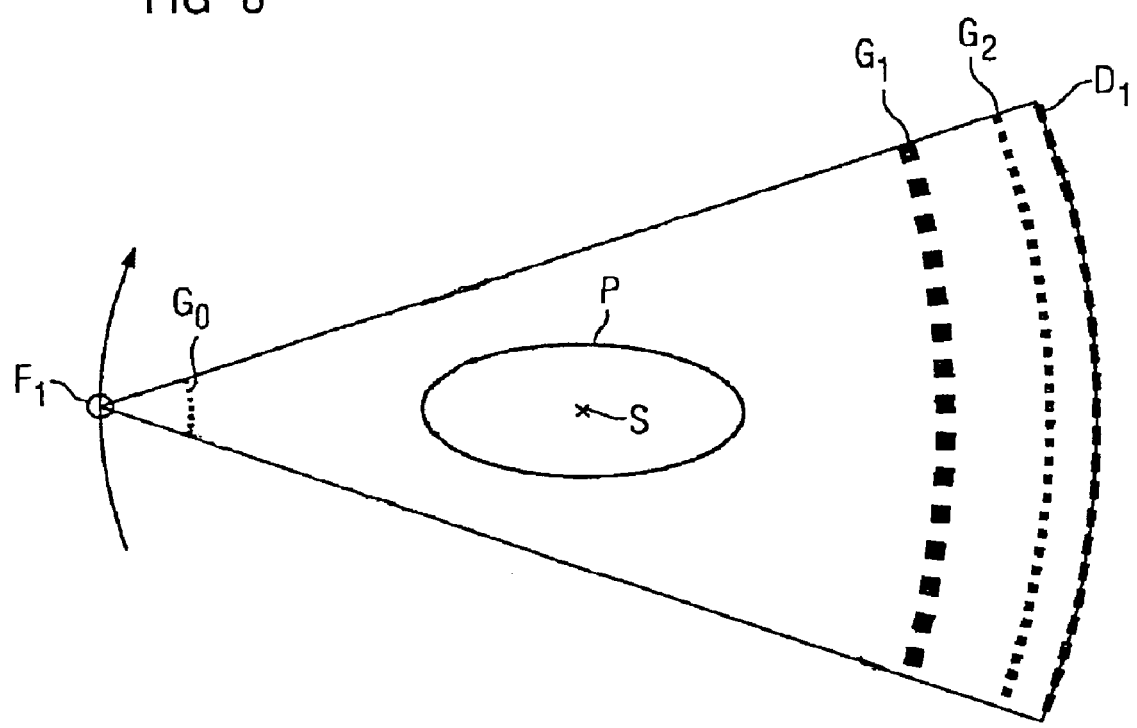
FIG. 8: shows a longitudinal section through a focus-detector system with the arrangement of the source grating, the phase grating and the analyzer grating according to another example embodiment.

FIG. 8 shows a longitudinal section through a focus-detector system with the arrangement of the source grating, the phase grating and the analyzer grating according to another example embodiment.

As shown in FIG. 8, the phase grating $G_1$ may have a radius of curvature around the focus $F_1$ in at least one section plane. In addition, the detector $D_1$ and/or the analyzer grating $G_2$ of the analysis-detector system may also have a curvature around the focus $F_1$.

In at least one focus-detector system, there is a grating according to an embodiment of the invention in which the grating structure, which is needed for the detection of phase contrast recordings, is generated in the grating medium by a standing ultrasound wave.

Moreover, it should also be pointed out that the focus-detector systems as presented are not only capable of measuring phase shifts of the X-radiation, which are caused by the sample or the patient, but are furthermore suitable for conventional measurement of the radiation absorption and the reconstruction of corresponding absorption recordings. Thus, combined absorption and phase contrast recordings may also be compiled. It is to be expressly pointed out that the medical application as presented merely represents an example application, and that the focus-detector arrangement according to the invention may also be used in the field of nondestructive material testing without restriction of generality.

In summary, it may therefore be stated that according to at least one embodiment of the invention as described, a focus-detector arrangement for X-ray phase contrast measurement has been presented which includes at least one grating tunable by ultrasound. Such a grating may have an ultrasound generator on one side and a reflector or a further ultrasound generator on the opposite side, so that grating structures are obtained which can be controlled flexibly through density variation or mass concentration variations by changing the ultrasound frequency and/or the spacing, or by a phase change between the excitation frequencies in the case of two generators.

It is to be understood that the features of the invention as mentioned above may be used not only in the combination respectively indicated, but also in other combinations or in isolation, without departing from the scope of the present invention.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A focus-detector arrangement of an X-ray apparatus for generating at least one of projective and tomographic phase contrast recordings of a subject, comprising:
   an X-ray source with a focus, arranged on a first side of the subject, to generate a beam of X-rays;
   a phase grating arranged on the opposite second side of the subject in the beam path, to generate an interference pattern of the X-radiation in a predetermined energy range; and
   an analysis-detector system to detect at least the interference pattern generated by the phase grating in respect of its phase shift with position resolution, wherein at least one grating of the focus-detector arrangement includes, at least partially, a macroscopically homogeneous medium which, when excited by an energy source, includes periodic structure variations that lead to interference phenomena when the X-ray beam passes through.

2. The focus-detector arrangement as claimed in claim 1, wherein a grating medium of the at least one grating comprises a gas.

3. The focus-detector arrangement as claimed in as claimed in claim 1, wherein a grating medium of the at least one grating comprises a liquid.

4. The focus-detector arrangement as claimed in claim 3, wherein the liquid is a suspension.

5. The focus-detector arrangement as claimed in claim 1, wherein a grating medium of the at least one grating is a gel.

6. The focus-detector arrangement as claimed in claim 1, wherein a grating medium of the at least one grating is a solid body.

7. The focus-detector arrangement as claimed in claim 6, wherein the solid body of the grating medium consists of a piezoelectric material.

8. The focus-detector arrangement as claimed in claim 1, wherein the energy source is ultrasound and wherein a grating medium of the at least one grating is arranged in a closed space, which comprises a first ultrasound generator on at least one side.

9. The focus-detector arrangement as claimed in claim 8, wherein the closed space of the grating medium of the at least one grating is bounded by an ultrasound reflector on the opposite side from the first ultrasound generator.

10. The focus-detector arrangement as claimed in claim 8, wherein the closed space of the grating medium of the at least one grating comprises a second ultrasound generator on the opposite side from the first ultrasound generator.

11. The focus-detector arrangement as claimed in claim 8, wherein hail the grating medium of the at least one grating is mechanically coupled to the first ultrasound generator on the at least one side.

12. The focus-detector arrangement as claimed in claim 1, wherein the at least one grating, formed by a grating medium excited with ultrasound, is the phase grating.

13. The focus-detector arrangement as claimed in claim 12, wherein the phase grating has at least one radius of curvature around the focus in at least one plane.

14. The focus-detector arrangement as claimed in claim 13, wherein the following geometrical relationship is satisfied for the period of an analyzer grating ($G_2$):

$$g_2 = \frac{1}{2} \cdot \frac{r_2}{r_1} \cdot g_1,$$

where:
$r_1$ = radial distance from the focus to the phase grating;
$r_2$ = radial distance from the focus to the analysis-detector system;
$g_1$ = period of the phase grating ($G_1$);
$g_2$ = period of the analysis-detector system for the phase detection.

15. The focus-detector arrangement as claimed in claim 14, wherein the following geometrical relationship is complied with:

$$r_1 > \frac{g_1^2}{2\lambda},$$

where:
$r_1$ = radial distance from the focus to the phase grating;
$g_1$ = period of the phase grating ($G_1$);
$\lambda$ = wavelength of the X-radiation.

16. The focus-detector arrangement as claimed in claim 13, wherein the following geometrical relationship is complied with:

$$r_1 > \frac{g_1^2}{2\lambda},$$

where:
$r_1$ = radial distance from the focus to the phase grating;
$g_1$ = period of the phase grating ($G_1$);
$\lambda$ = wavelength of the X-radiation.

17. The focus-detector arrangement as claimed in claim 13, wherein the following geometrical relationship is complied with as the distance d between the phase grating and an analyzer grating:

$$r_2 - r_1 = d_m = \left(m - \frac{1}{2}\right) \cdot \frac{g_1^2}{4 \cdot \lambda},$$

where:
$r_1$=radial distance from the focus to the phase grating;
$r_2$=radial distance from the focus to the analysis-detector system;
$g_1$=period of the phase grating ($G_1$);
$d_m$=distance from the phase grating to the analysis-detector system=$m^{th}$ order Talbot distance;
$\lambda$=wavelength of the X-radiation.

18. The focus-detector arrangement as claimed in claim 1, wherein the focus is of substantially point-like design and the following coherence condition is fulfilled:

$$L = \lambda \frac{r_1}{s} > g_1,$$

where:
$r_1$=radial distance from the focus to the phase grating;
s=transverse source size;
$g_1$=period of the phase grating ($G_1$);
$\lambda$=wavelength of the X-radiation.

19. The focus-detector arrangement as claimed in claim 18, wherein a source grating for generating a beam of coherent rays is arranged between the focus and the subject.

20. The focus-detector arrangement as claimed in claim 19, wherein the energy source is ultrasound and wherein the at least one grating, formed by a grating medium excited with ultrasound, is the source grating.

21. The focus-detector arrangement as claimed in claim 1, wherein the analysis-detector system is formed as a combination of a position-resolving detector having a multiplicity of detector elements, which determine the position resolution of the system, and an analyzer grating upstream in the radiation direction for determining the average phase shift of the X-radiation of a particular energy per detector element.

22. The focus-detector arrangement as claimed in claim 21, wherein the detector of the analysis-detector system has a curvature around the focus.

23. The focus-detector arrangement as claimed in claim 22, wherein the analyzer grating of the analysis-detector system has a curvature around the focus.

24. The focus-detector arrangement as claimed in claim 21, wherein the energy source is ultrasound and wherein the at least one grating, formed as an ultrasound-induced grating, forms the analyzer grating.

25. A method for operating an X-ray system for generating at least one of projective and tomographic phase contrast recordings, comprising:
using the focus-detector arrangement as claimed in claim 24; and
using, for measuring the phase shift of the X-radiation in the analysis-detector system, a relative displacement, necessary for measuring the phase shift, between at least one of gratings and the detector system and gratings and a focus, a phase angle of the ultrasound-induced grating being controlled.

26. The focus-detector arrangement as claimed in claim 21, wherein the analyzer grating of the analysis-detector system has a curvature around the focus.

27. The focus-detector arrangement as claimed in claim 1, wherein the analysis-detector system is formed as a position-resolving detector having a multiplicity of detector elements, which determine the position resolution of the system.

28. An X-ray system for generating projective phase contrast recordings, comprising a focus-detector arrangement as claimed in claim 1.

29. An X-ray C-arc system for generating projective or tomographic phase contrast recordings, comprising a focus-detector arrangement as claimed in claim 1.

30. An X-ray CT system for generating tomographic phase contrast recordings, comprising a focus-detector arrangement as claimed in claim 1.

* * * * *